United States Patent [19]

Rosenthal et al.

[11] 4,286,327

[45] Aug. 25, 1981

[54] APPARATUS FOR NEAR INFRARED QUANTITATIVE ANALYSIS

[75] Inventors: Robert D. Rosenthal; Scott B. Rosenthal, both of Gaithersburg, Md.

[73] Assignee: Trebor Industries, Inc., Gaithersburg, Md.

[21] Appl. No.: 73,965

[22] Filed: Sep. 10, 1979

[51] Int. Cl.³ ............... G06F 15/20; G01N 21/00; G01J 3/48
[52] U.S. Cl. ................... 364/498; 364/497; 250/338; 356/416
[58] Field of Search .............. 364/496–499, 364/526; 250/338, 341, 343, 345; 356/416, 418

[56] References Cited

U.S. PATENT DOCUMENTS

| | | | |
|---|---|---|---|
| 3,734,631 | 5/1973 | Justice et al. | 250/345 |
| 3,776,642 | 12/1973 | Anson et al. | 364/497 |
| 3,828,173 | 8/1974 | Knepler | 364/498 |
| 3,996,599 | 12/1976 | King | 250/338 |
| 4,035,643 | 7/1977 | Barrett | 250/343 |
| 4,190,851 | 2/1980 | Finnila et al. | 250/338 |
| 4,207,466 | 6/1980 | Drage et al. | 250/338 |

OTHER PUBLICATIONS

"An Introduction to Near Infrared Quantitative Analysis" Presented by R. Rosenthal at the 1977 Annual Meeting of American Association of Cereal Chemist.
"Fat Measurement of Ground Beef with a Gallium Arsenide Infrared Emitter" by D. R. Massie, Published in ASAE Publication, 1976.

Primary Examiner—Charles E. Atkinson
Assistant Examiner—Gary Chin
Attorney, Agent, or Firm—Sughrue, Rothwell, Mion, Zinn and Macpeak

[57] ABSTRACT

An apparatus for near infrared quantitative analysis with an infrared emitting diode (IRED) source utilizes narrow bandpass filters and silicon detectors to provide highly accurate and inexpensive measurement. A narrow bandpass filter in the light path of the IRED passes wavelengths outside the half power bandwidth points of the IRED. A silicon detector together with a sensitive amplifier is used to accurately measure linearly up to six decades of light sensitivity at desired wavelengths.

7 Claims, 2 Drawing Figures

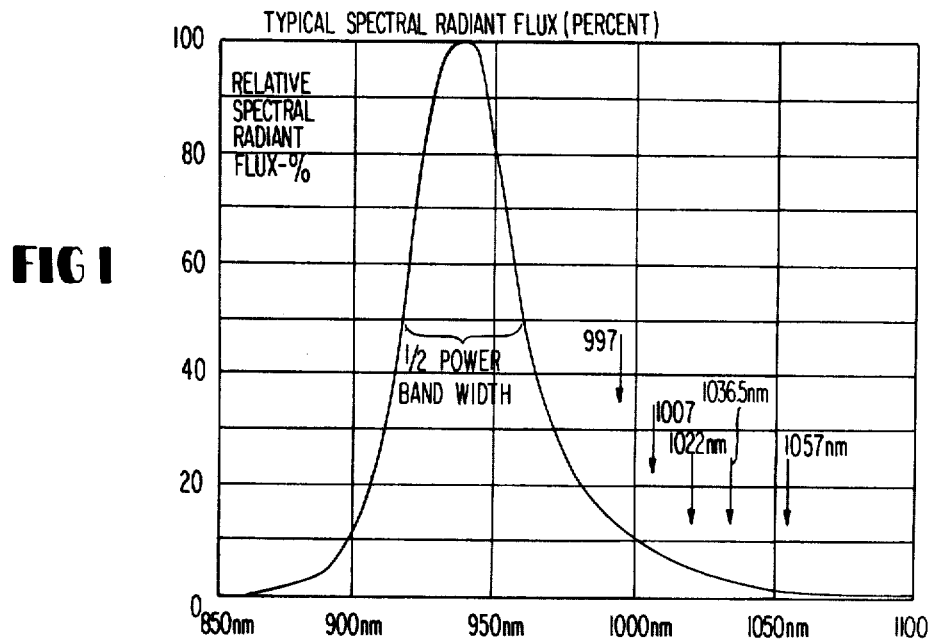
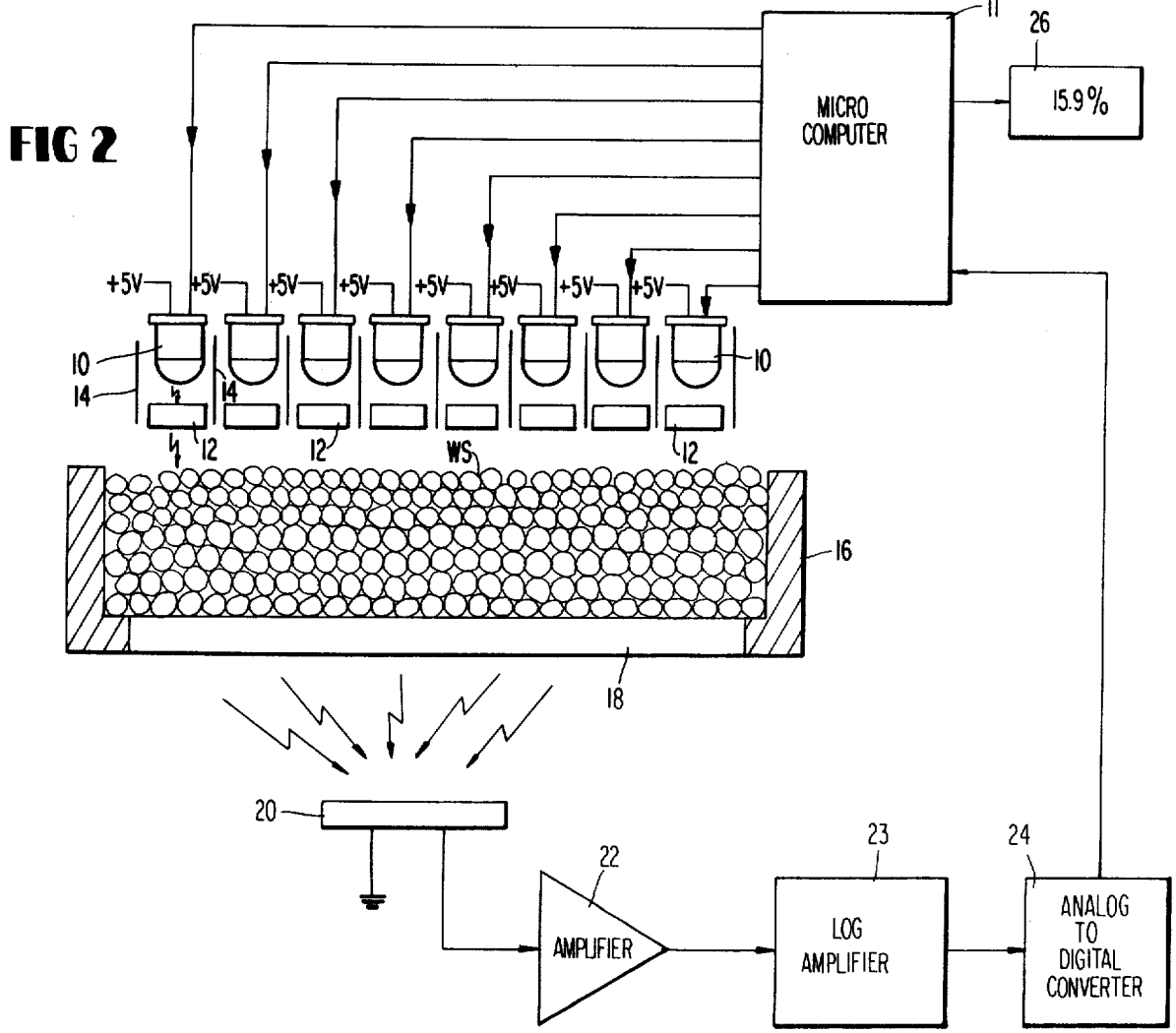

APPARATUS FOR NEAR INFRARED QUANTITATIVE ANALYSIS

BACKGROUND OF THE INVENTION

1. Field of the Invention

The invention relates to improvements in apparatus for near infrared (NIR) analysis for measuring chemical constituents in a quantitative fashion. More particularly, the improvements of this invention allow accurate measurements with inexpensive instruments.

2. Prior Art

There are known in the prior art instruments which measure chemical constituents in a product by means of either reflecting near infrared radiant energy off the product or transmitting infrared energy through the product. These instruments use the phenomenon that certain organic substances absorb energy in the near infrared portion of the spectrum. By measuring the amount of energy absorbed by the product at certain specific wavelengths, precise quantitative measurements of the constituents in a product become available. For example, the measurement of protein content in wheat can be performed in this manner. For general introduction to near infrared quantitative analysis, see the paper presented by Robert D. Rosenthal to the 1977 Annual Meeting of American Association of Cereal Chemists entitled "An Introduction to Near Infrared Quantitative Analysis". Such analysis can be performed on samples within only a few seconds without special sample preparation except for grinding the sample.

Current commercial near infrared instruments use the same generic technology for developing the near infrared energy. The commercial instruments use a tungsten light source that provides radiant energy through the visible, the near infrared as well as the longer infrared portions of the spectrum. This broad spectrum of energy is modified by the use of narrow band optical filters (or gratings or prisms) to allow only a small selected portion of the total spectrum to fall on the object being measured. Thus, the current instruments are not efficient in the use of illuminating energy because only such a very small portion of the total energy provided by the tungsten lamp is used in the measurement. The great majority of the radiated energy from the tungsten lamp is deliberately not used and is dissipated to heat. This causes temperature problems and other penalties in instrument design.

The instrument laboratory of the U.S. Department of Agriculture in Beltsville, Maryland several years ago, performed studies on the use of another type of "light source". In those studies infrared emitting diodes (IRED's are solid state devices that yield energy at very narrow regions of the spectrum compared to a conventional tungsten bulb) were used. The U.S.D.A. work was summarized in the technical paper entitled "Fat Measurement of Ground Beef with a Gallium Arsenide Infrared Emitter" (ASAE publication 1-76 "Quality Detection in Foods"). In the U.S.D.A.'s technical paper there is mentioned the possibility of narrowing the region of infrared energy by putting narrow bandpass filters in front of the IRED. This, however, was directed to an effort for measurement of wavelengths between 920 and 970 nanometers (nm).

In 1978 U.S.D.A. research discovered that precise measurement of the constituents in grain (e.g., protein) can be made at wavelengths slightly longer than discussed in the 1976 paper. The desired wavelengths for protein measurement in grain are between 1000 and 1060 nm.

Previously protein measurement in grain required measurement at wavelengths above 1200 nm. These longer wavelengths forced the use of poor performing PbS light detectors. Thus, the U.S.D.A. discovery that precise measurement of protein in grain can be wavelengths shorter than 1200 nm appears to be of great value because it allows the use of lower cost, and more stable, silicon detectors.

The U.S.D.A. began to search for IREDs with center wavelengths between 1000 and 1060 nm. Unfortunately, only very expensive indium gallium agenide IRED's are available in this wavelength. Conventional IREDs of gallium arsenide provide peak energy well below 1000 nm; normally about 940 nm. Therefore, although the conventional IREDs are of low cost (about a third of 1% of the indium gallium arsenide IRED's) they are not considered useful for protein measurement because the half power bandwidth was limited to between 910 and 970 nm. Half power bandwidth refers to the wavelength that has one-half of the output power as the center wavelength. Normally, IREDs are never used outside the half power bandwidth points.

SUMMARY OF THE INVENTION

This invention utilizes a combination of the properties of conventional IREDs and of silicon detectors to allow the conventional low cost IREDs to be used outside their half power bandwidth up to (at least) 1060 nm. Conventional IREDs that have a peak radiation at 940 nm only emit about 1 to 10% of their power at 1000 nm as the wavelength gets longer, toward 1060 nm, the amount of energy radiated falls even lower.

Silicon detectors are well known for having the unique property of being sensitive and linear over seven decades of light level. This invention, involving the combining of a conventional IRED and silicon detector allow six decades of light sensitivity at wavelengths between 1000 and 1060 nm to be measured linearly.

In specific application, a narrow bandpass optical filter is positioned in the light path of a conventional IRED and the energy transmitted through the narrow bandpass is measured with a silicon detector which together with sensitive amplifiers (e.g., logarithmic amplifiers) allows the IRED to provide a specific measurement wavelength of up to 1060 nm.

In some cases, many wavelengths are simultaneously needed. Thus, the preferred embodiment of the invention includes multiple numbers of IREDs each with its own specific bandpass filter. The IREDs are rippled, i.e., turned on one at a time consecutively, thereby allowing a single silcon detector to measure many wavelengths. The IRED has low cost and extemely low power dissipation property. Thus, this invention having for example 12 IREDs, the total power dissipation is still less than 1% of what would be used with a normal tungsten lamp of the prior art.

BRIEF DESCRIPTION OF THE DRAWINGS

FIG. 1 is a curve of a typical, spectral radial flux from a commerical infrared emitting diode showing the five wavelengths required for wheat protein measurement;

FIG. 2 illustrates a preferred embodiment of an apparatus of this invention;

DETAILED DESCRIPTION OF THE PREFERRED EMBODIMENT

The preferred embodiment will be described with regard to making accurate protein measurements of wheat by means of the magnitude of near infrared light absorbed passing through the wheat.

Research at the U.S. Department Agriculture (U.S.-D.A.) has shown that the protein content of wheat can be measured by transmitting selective wavelengths of near infrared light through the wheat and determining the magnitude of light absorbed at each of selected wavelengths. The USDA research demonstrated that accurate protein measurement can be made using the following algorithm:

Percent Protein =

$$k_0 + k_1 \left( \frac{\log \frac{1}{T_1} - 2 \log \frac{1}{T_2} + \log \frac{1}{T_3}}{\log \frac{1}{T_4} - 2 \log \frac{1}{T_2} + \log \frac{1}{T_5}} \right)$$

where:

$K_o$ and $K_1$ are proportionality constants;
$T_1$ = percent light transmitted through the wheat sample at 1007.5 nanometers (nm);
$T_2$ = percent light transmitted through the wheat sample at 1022 nm;
$T_3$ = percent light transmitted at 1036.5 nm;
$T_4$ = percent light transmitted at 997 nm;
$T_5$ = percent light transmitted at 1057 nm.

FIG. 1 shows the spectrum distribution of the light emitted by typical commerical infrared emitting diodes (IRED). Also shown in FIG. 1 are the five wavelengths required for wheat protein measurement. Most of the required wavelengths are in the region where the IRED emits very little optical energy. However, a finite amount of usable energy is still emitted at such wavelengths even though the wavelengths are outside the half power bandwidth points of the IRED as shown in FIG. 1.

FIG. 2 illustrates the preferred embodiment in schematic form.

In FIG. 2 eight commerical IREDs 10 are sequentially pulsed on and off by signals from a microprocessor 11. The microprocessor is programmed to allow only one of the IREDs to be turned on at a time and automatically sequences through all eight IREDs. In addition the time the IRED is on is controlled by the microprocessor. The IREDs are pulsed so that they are driven with much more current than in a DC state. This is necessary because of the small amount of optical energy that is radiated at the wavelengths of interest.

The infrared light emitted from each IRED 10 is transmitted through an accompanying narrow bandpass optical filter 12. The optical filter 12 absorbs all wavelengths of light except those near its center wavelength. These eight filters all have different center wavelengths. Five are used for wheat protein measurement wavelengths of FIG. 1 and the remaining three wavelengths are used to measure additional parameters such as the moisture content of wheat. Light baffles 14 between each set of IREDs and narrow bandpass filters prevent the light from one IRED being transmitted through an adjacent narrow bandpass filter.

Each of the specific wavelengths are transmitted through a wheat sample WS that is held in an opaque cup 16. The cup has a glass bottom 18 so that the light energy can pass through and impact on a silicon photodetector 20. This silicon detector is especially designed to measure extremely low light levels. The light impacting on the silicon detector is converted by the detector into an electrical current which is amplified by a low noise amplifier 22. The output of this amplifier is fed to and further amplified by a log amplifier 23. The amplified signal is then converted to a digital signal for inputting into a microcomputer by means a 12 bit analog-to-digital converter 24.

The microprocessor 11 records in its memory the amount of transmitted energy obtained from each of the IREDs. It then uses the equation set forth above to calculate the amount by weight of protein in the sample of wheat. The result is displayed on a digital meter 26 built into the instrument.

The combination of the microprocessor and the IRED array allows large numbers of measurements to be made and simultaneously averaged in less than a second to thereby reduce error as compared to using a single or small number of like measurements.

In one specific example in an instrument constructed in accordance with this invention, the IREDs 10 are General Electric Company part No. 1N6264. The microprocessor 11 is an Intel 8085 system. The silicon detector 20 is a Silicon Detector Corporation part SD-444-11-11-251. The amplifier 22 is an Analog Devices Corp. AD517, the log amplifier 23 is an Analog Devices Corp. AD755N, and the analog-to-digital converter 24 is an Analog Devices Corp. AD574. Although the preceding discussion described a system using a silicon detector, other types of detectors with similar operating characteristics can be used, e.g., cadmium sulfide, or germanium.

What is claimed is:

1. An apparatus for near infrared quantitative analysis comprising:
   a plurality of pulsed infrared emitting diodes (IREDs) of specific one-half power bandwidth;
   means for providing pulses to control the on off status of the IREDs;
   a highly sensitive infrared detector positioned to receive infrared energy reflected or transmitted through a sample;
   a plurality of stationary bandpass filters each selected to allow passage of a preselected wavelength band through it, which selected band is outside the one-half power bandwidth of the IRED, each of the said bandpass filters positioned between each of the said IREDs and the infrared detector;
   means for preforming the said quantitative analysis based on the energy received by said infrared detector.

2. An apparatus as defined in claim 1, wherein the detector is a silicon detector and further comprising a sensitive amplifier connected to the silicon detector.

3. An apparatus as defined in claim 1, wherein each of the IREDs are turned on one at a time consecutively and are detected by a single silicon detector.

4. An apparatus as defined in claim 3, wherein a microprocessor is used to control the IREDs and provide a large number of averaged measurements in less than a second.

5. An apparatus as defined in claim 4 wherein the microprocessor utilizes the amplified output of the silicon detector to compute with a preselected algorithm and includes means to display the results of the computation.

6. An apparatus as defined in claim 5 wherein the preselected wavelength bands of the band pass filters include wavelengths of 997, 1007, 1022, 1036.5 and 1057 nm.

7. An apparatus as claimed in claim 1 further comprising an amplifier connected to a silicon detector feeding a logarithmic amplifier whose output in turn is converted to digital signals used to input a microprocessor.

* * * * *